(12) United States Patent
Rutschmann et al.

(10) Patent No.: US 8,363,927 B2
(45) Date of Patent: Jan. 29, 2013

(54) HIGH-RESOLUTION OPTICAL DETECTION OF THE THREE-DIMENSIONAL SHAPE OF BODIES

(75) Inventors: Dirk Rutschmann, Stuttgart (DE); Rene Pfeiffer, Markgroningen (DE)

(73) Assignee: corpus.e AG, Stuttgart (DE)

( * ) Notice: Subject to any disclaimer, the term of this patent is extended or adjusted under 35 U.S.C. 154(b) by 239 days.

(21) Appl. No.: 12/742,763

(22) PCT Filed: Nov. 19, 2007

(86) PCT No.: PCT/EP2007/009993
§ 371 (c)(1),
(2), (4) Date: Jul. 13, 2010

(87) PCT Pub. No.: WO2009/065418
PCT Pub. Date: May 28, 2009

(65) Prior Publication Data
US 2010/0296726 A1 Nov. 25, 2010

(51) Int. Cl.
*G06K 9/00* (2006.01)
(52) U.S. Cl. .................. 382/154; 382/100; 382/285
(58) Field of Classification Search .................. 382/100, 382/154, 285; 702/167; 356/12, 601, 625; 600/592; 345/420, 419, 427
See application file for complete search history.

(56) References Cited

U.S. PATENT DOCUMENTS

2003/0137510 A1 7/2003 Massen
2005/0168756 A1* 8/2005 Massen .................. 356/601
2007/0288198 A1* 12/2007 Massen et al. ............ 702/167

FOREIGN PATENT DOCUMENTS

| DE | 195 36 294 A1 | 4/1997 |
|---|---|---|
| DE | 101 56 908 A1 | 5/2003 |
| DE | 203 01 177 U1 | 6/2003 |
| DE | 10 2004 007 455 A1 | 9/2005 |
| DE | 10 2005 051 020 A1 | 4/2007 |
| EP | 1 322 911 B1 | 12/2006 |
| WO | WO-2004/078040 A1 | 9/2004 |

OTHER PUBLICATIONS

Webpage document downloaded from www.vitus.de, in English discloses an Vitronic PEDUS 3D foot scanner.
Webpage document downloaded from www.breuckmann, in English discloses a body SCAN 3D body scanner.
Webpage document downloaded from www.corpus.e.com, in English discloses a lightbeam 3D foot scanner.

* cited by examiner

*Primary Examiner* — Ali Bayat
(74) *Attorney, Agent, or Firm* — Tarolli, Sundheim, Covell & Tummino LLP

(57) ABSTRACT

In a cost-efficient method and arrangement for 3D digitization of bodies and body parts, which produces dense and exact spatial coordinates despite imprecise optics and mechanics, the body to be digitized is placed on a photogrammetrically marked surface, a photogrammetrically marked band is fitted to the body or body part to be digitized, and a triangulation arrangement comprised of a camera and a light pattern projector is moved on a path around the body. By a photogrammetric evaluation of the photogrammetric marks of the surface and the band situated in the image field of the camera, and of the light traces of the light projector on the marked surface and the marked band, all unknown internal and external parameters of the triangulation arrangement are determined, and the absolute spatial coordinates of the body or body part are established from the light traces on the non-marked body with high point density and high precision without any separate calibration methods.

12 Claims, 2 Drawing Sheets

HIGH-RESOLUTION OPTICAL DETECTION OF THE THREE-DIMENSIONAL SHAPE OF BODIES

FIELD OF THE INVENTION

The invention relates to a method for precise optical detection of the 3D spatial shape of bodies and body parts, and to an arrangement for implementing such method.

BACKGROUND OF THE INVENTION

The detection of the three-dimensional spatial shape of bodies or body parts, in particular of human body parts, such as legs, torso or feet, is an important aspect in the production or assignment of fitting articles of clothing, orthopedic aids such as compression stockings, prostheses and ortheses and also in the production or assignment of fitting shoes. Numerous optical 3D scanners are on the market, most of which operate either on the basis of the methods of laser triangulation (see, e.g., PEDUS foot scanner of the company of Vitronic Dr. Stein, www.vitus.de) or stripe projection (see, e.g., bodyScan of the Breuckmann company, www.breuckmann.com). Both methods are based on triangulation, i.e. a stable spatial triangular arrangement of a light projector, a camera and a body for point-by-point determination of the distance of the body surface observed from the triangulation arrangement made up of the camera and the light projector, also referred to as measuring head. An XYZ point model of the surface viewed is determined from the sum of this distance data. In order to detect the entire body, either a plurality of camera/projector arrangements need to be mounted and/or moved around the body (e.g., in the case of the bodyScan of the Breuckmann company) or a camera/projector arrangement needs to be mechanically moved over the body surface (as in the case of the PEDUS foot scanner of the Vitronic Dr. Stein company, for example).

The angular arrangement of the camera/projector is sensitive: even small angle errors result in large errors of measurement in the distances measured. The movement of the triangulation arrangement in the space is equally sensitive: small errors in the position determination of the measuring head result in large errors of measurement in the 3D point model generated. This sensitivity results in that, even in case of a very sturdy and involved opto-mechanical construction, these scanners require frequent recalibration, in particular also after each transportation and upon each movement of the scanner. In addition, since these scanners frequently also carry the weight of the customer (e.g., in the case of the pedus foot scanner), the requirement of a rigid design can only be met with considerable expense, so that under this aspect as well, calibration needs to be repeated frequently.

Calibration of a 3D scanner operating on the basis of triangulation using laser or stripe projection with the aid of different normal lines provides a large number of parameters which directly determine the measuring accuracy. These include:

the exact spatial position between the camera and the projector (triangulation angle, base line, mutual orientation, etc.);

the exact internal parameters of the camera and the projector (focal lengths, sensor dimension, geometry of the picture elements, tilt angle and angle of rotation of the laser line projector, etc.);

the exact spatial positions of the triangulation arrangement for each measuring image taken, the so-called external parameters.

Therefore, calibration of a 3D scanner is a complicated process which is to be carried out with the aid of high-precision calibration bodies and which in many cases is asking too much of the sales staff of, e.g., an orthopedic specialist store and is therefore not accepted.

Because of the mechanical stability required, these 3D scanners cannot be offered at a particularly low price, either, so that many potential applications of the so-called mass-customization (the production of individually fitting clothing and the like) are not currently implemented due to the high costs of the 3D scanners.

The company of corpus.e AG (www.corpus-e.com) has developed a photogrammetric foot scanner under the name "Lightbeam®", which operates without a projector and thus also without a sensitive triangulation arrangement. Here, the foot is covered with a specially marked, elastic sock and a video camera is mechanically moved around the foot (see also WO 2004/078040 A1). The foot is placed on a photogrammetrically marked support, so that the spatial position from which the camera measures can be permanently automatically determined using the methods of photogrammetry (the so-called "external" parameters of a photogrammetric measuring arrangement). Likewise, the so-called "internal" parameters of the camera itself, such as focal length, image sensor, piercing point of the optical axis, lens distortions, etc. can be determined automatically from the evaluation of overlapping 2D exposures of the marked support and the marked foot. This makes this system completely calibration-free. It may be put into operation after transportation at any time without calibration; there is no need to ever recalibrate it after a change of load; the structure may be of a simple and inexpensive design in terms of mechanical stability since the latter does not contribute to the final result, the 3D model measured.

There is, however, a drawback inherent in this otherwise powerful method: due to the density, which is limited by constitution, of the photogrammetric markings on the elastic sock, the density of the XYZ point cloud generated is distinctly lower in comparison with a laser or stripe projection method (typically 4000 XYZ points as against approx. 1 million XYZ points). While this lower point density does not constitute a disadvantage in the case of flat body parts such as the upper foot, it is critical in regions of high spatial curvatures such as in the region of the toes, the heel, the transition from the upper foot to the sole, etc.

The requirement that the body to be measured needs to be covered with a photogrammetrically marked, elastic covering constitutes a further drawback. Such coverings are not simple to produce; depending on the body part, such as the torso, legs, feet, etc., several shapes and sizes are needed.

It may also be important that, when a customer's feet are digitized for the selection of suitable ski boots, for example, the customer keeps on his/her own winter sock, for the sock to be taken into consideration in the shape adaptation. But it is not possible to photogrammetrically mark any random sock using simple means.

There is therefore a great economic and technical interest in providing a 3D digitizer which does not require any complicated calibration and which generates a density of spatial points without the requirement of using a photogrammetrically marked, elastic covering. The 3D digitizer should thus be cost-efficient, high-resolution, and calibration-free or self-calibrating.

SUMMARY OF THE INVENTION

In accordance with the invention, the method for precise optical detection of the 3D spatial shape of bodies or body parts by digital scanning comprises the steps of: (i) positioning a body to be scanned or a body part to be scanned on a surface of a base, the surface being marked with photogrammetric marks; (ii) applying photogrammetric marks in a partial area of the body or body part; (iii) moving a triangulation arrangement around the body or body part, the triangulation arrangement including a camera and a light pattern projector; (iv) the camera capturing a sequence of images and the light pattern projector projecting a light pattern onto the body or body part; (v) wherein each captured image includes an image field extending from the marked surface over non-marked areas of the body or body part, the photogrammetric marks are attached to the body or body part such that they are captured at least in the majority of captured images, the photogrammetric marks are attached to the body or body part such that they are captured in an area of the image field opposite the marked surface, and the image fields of successive captured images overlapping each other; (vi) evaluating the photogrammetric marks of the surface and the photogrammetric marks and the light pattern of the light projector on the marked surface and in the area of the photogrammetric marks to determine internal and external parameters of the triangulation arrangement for each position in which an image was captured; and (vii) determining the 3D spatial shape of the body or body part by applying methods of photogrammetry using these parameters and by evaluating the position of the light pattern on the body or body part in the images taken by the camera.

Thus, an evaluation of the photogrammetric marks of the surface and the marks on the body as well as of the light pattern of the at least one light projector on the marked surface and in the area of the marks on the body, the internal and external parameters of the at least one triangulation arrangement are co-determined for each image capturing position in each image capturing process. All internal and external parameters of the measuring head consisting of the camera and the light projector are thus automatically determinable using photogrammetric methods, more specifically simultaneously with the 3D measurement proper, without a separate, complicated calibration procedure using a calibration body being required. In doing so, the parameters of the camera are determined by evaluation of the photogrammetric marks and the parameters of the triangulation arrangement by evaluation of the position of the light trace on the marked surface and of the body region provided with marks in relation to the marks. Using the parameters determined in this way and using methods of photogrammetry, the 3D spatial shape of the body or body part is then determined by evaluation of the position of the light pattern on the body or body part in the images captured by the at least one camera. Since the parameters are co-determined each time, the demands on the stability of the triangulation arrangement are low and the mechanical guide and the drive may be configured to be very simple and favorably priced, since the mechanical accuracy thereof does not influence the accuracy of the photogrammetric determination of the camera position.

In order to obtain stable values for the self-calibration, it is of advantage if photogrammetric marks are distributed over the entire image field. But it is awkward in the case of a simple and easily accessible digitizer to arrange further marked surfaces in the background of the upper image field. The depth of field would not be sufficient and the entire volume of the 3D digitizer would be too large for many orthopedic stores. Therefore, in accordance with the invention, photogrammetric marks are applied in a partial area of the body in the upper area; in a preferred embodiment, these photogrammetric marks are applied on a narrow, elastic band which in turn is fitted to the body or body part itself in the upper area, i.e. such that the band is as far away from the marked surface as possible. The multiple detection of the marks on the surface and the band allows a substantially more stable bundle adjustment and, hence, a more reliable calculation of the internal and external parameters of the camera. The marked band is also required to determine a possible tilt angle of the light line of the projector. In comparison with having to completely clothe the entire body with a photogrammetrically marked, elastic covering, the marking in the form of an inexpensive narrow band constitutes a great simplification. In addition, the surface of the body/body part that is actually of interest remains free for a high-resolution 3D digitization in accordance with the number of evaluated light sections, therefore resulting in the generation of a very dense XYZ point cloud of the body to be digitized. It will be understood that forms of applying the marks other than using a band are also conceivable.

In order to obtain a calibration-free or self-calibrating 3D digitizer, which preferably operates according to the light section procedure, it is not sufficient to know the internal and external parameters of the camera alone. The spatial positions of the light line projector, which is mounted in a triangulation arrangement with the camera, also need to be known, in particular the angle between the optical axis of the camera and that of the projector, the vertical spatial position of the projected light line, and the camera-projector distance, the so-called base line of the triangulation.

These unknown parameters are obtained in accordance with the invention by the evaluation of the positions of the light traces in the camera images, which produces the projected light line on the marked surface and the marked band and/or in the region of the marks applied.

According to the invention, based on this self-calibration the entire 3D digitizer is cost-efficient to manufacture since all of the mechanical components need to be designed and produced simply and only with moderate mechanical stability and accuracy.

Since the photogrammetric self-calibration is carried out continuously along with the actual digitization of the foot, the object according to the invention of providing a very cost-efficient, self-calibrating and high-resolution 3D digitizer is thus achieved, which, except for additional photogrammetric marks on the body, applied by means of a simple elastic band, for example, manages without a photogrammetric marking of the body to be digitized.

A further advantage consists in that the photogrammetric marks of the surface and on the body (preferably on a band) may be configured purely in black and white. Owing to its high brightness, the projected light pattern or light line can be easily recognized in the image of a black-and-white camera. The method according to the invention does therefore not require a color camera, which again constitutes a considerable simplification and cost reduction.

It will be understood that the method according to the invention may not only be employed for biological, but also for technical or artistic bodies, such as for the digitization of artistically valuable sculptures, of cast bodies and the like. The concept of the invention also covers methods in which the light projector generates not only a simple line, but more complex light patterns, such as, e.g., a plurality of parallel lines, lines encoded wing colors or black and white. Such light pattern projectors are known to those of ordinary skill in the art of image processing.

Furthermore, it is also known to configure a triangulation measuring head in such a way that one light pattern projector each is arranged on ether side of a single camera; in particular concave spatial shapes can be better detected thereby.

Advantageously, the triangulation measuring head may also be moved manually, i.e. without a mechanical guide, around the body to be digitized; in doing so, it should merely be made sure that for each taking position, the image field of the camera extends from the marked surface over the body to be digitized as far as to and including the markings on the body, even though, depending on the shape of the body, there may be individual taking positions in which the band is concealed.

What is essential to the concept of the invention is that by way of the method according to the invention of self-calibration of the moving camera and the light projector moved along, all internal and external parameters of the entire measuring head and of the entire structure are determined automatically, continuously and simultaneously with the 3D scanning of the body, on the basis of the evaluation of the photogrammetrically marked surface and of the preferably used photogrammetric band also captured by the camera in addition to the light line, as well as of the light trace of the light projector on the marked surface and the marked band, as a result of which no complicated separate calibration whatsoever is required for the digitizer according to the invention.

The method and the arrangement according to the invention therefore permit the construction of very cost-efficient and yet precise and high-resolution self-calibrating 3D digitizers in comparison with the prior art.

BRIEF DESCRIPTION OF THE DRAWINGS

Further features and advantages of the invention are taught in the accompanying dependent claims and will be apparent from the description of an example of use, which describes a 3D digitizer for a foot, with reference to the following illustrations:

DESCRIPTION OF PREFERRED EMBODIMENTS

Figure 1:
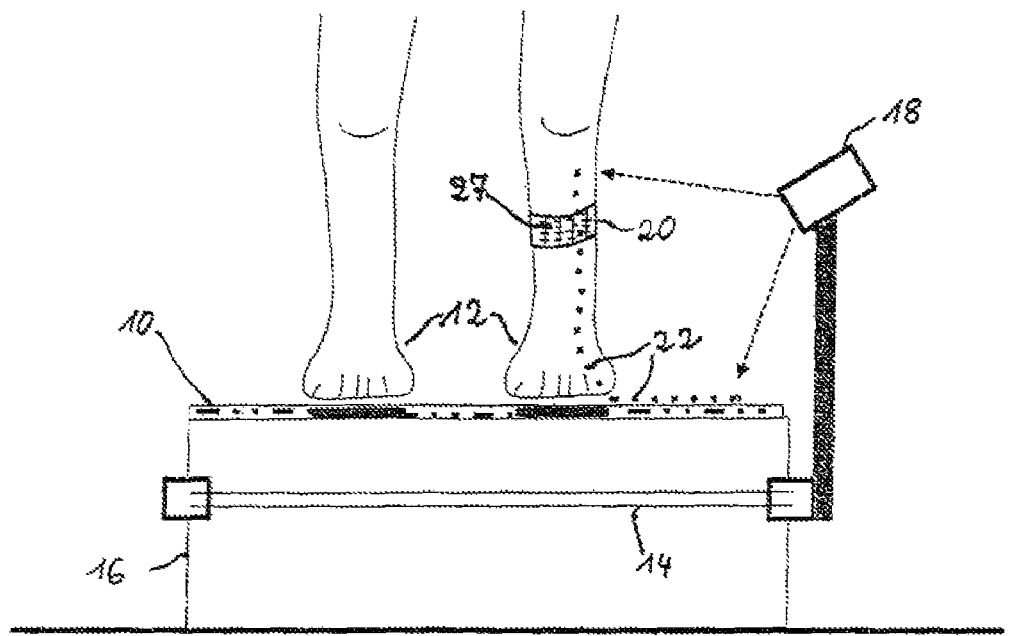
FIG. 1 shows a side view of an arrangement according to the invention in principle.

The exemplary embodiment selected describes the 3D digitization of a foot, for example for the production of an adapted orthopedic shoe. FIG. 1 shows a side view of a photogrammetrically marked surface 10 on which a patient stands, with his feet 12 being visible. A triangulation arrangement 18 with a camera and a light line projector can be mechanically moved around the patient along a substantially circular guide 14 which is mounted to a support 16. Instead of a light line projector, use may also be made of a projector that projects a more complicated light pattern. The mechanical arrangement may be of a simple design; a manual movement of the triangulation arrangement without a guide is also possible. A narrow, preferably elastic, photogrammetrically marked band 20 is in tight fitting contact with a leg above the foot to be digitized; it will be understood that a respective band can also be fitted to each foot, or some other form of applying the marks may be selected as well. The band 20 is fitted such that it is located on the upper border of the image field only just detected by the camera, i.e. it is detected in an area of the image field that is opposite to the marked surface, in order to obtain stable calibration values thereby. Suitable automatically evaluatable photogrammetric markings, which are easy to manufacture in the form of knitted textiles, for example, are described in EP 01 986 759.7.

In an exemplary embodiment, a black-and-white camera is involved, and the design of the shape and/or brightness of the marks of the surface 10 and of the band 20 as well as of the light pattern projector are selected such that they can be recognized and distinguished in the gray scale value images of the black-and-white camera using known methods of optical pattern recognition. In another exemplary embodiment, a black-and-white camera is involved, and the design of the shape and/or brightness of the marks (26) of the surface (10) and of the photogrammetric marks (27) as well as of the light pattern projector (30) are selected such that they can be recognized and distinguished in the gray scale value images of the black-and-white camera using the methods of optical pattern recognition. It is, however, also possible to use a color-capable camera and to select the colors of the photogrammetric marks of the surface 10 and of the band 20 and the color or colors of the light pattern projector such that they can be recognized and distinguished in the color images of the color camera using the methods of color classification.

In the case of a color camera, according to one exemplary embodiment, the colors of the photogrammetric marks of the surface and of the band and the color or colors of the light pattern projector as well as the design of the shape and/or brightness of the marks of the surface and of the band and of the light pattern projector may also be selected such that they can be recognized and distinguished in the color images of the camera using the methods of optical pattern recognition. In case of a color camera, according to another exemplary embodiment, the colors of the photogrammetric marks (26) of the surface (10) and of the photogrammetric marks (27) as well as the color or colors of the light pattern projector (30) and the design of the shape and/or brightness of the marks of the surface and of the band as well as of the light pattern projector are selected such that they can be recognized and distinguished in the color images of the color camera using the methods of optical pattern recognition.

When it is intended to determine the surface characteristics of the body as well, the light pattern projector is switched over preferably alternately between a patternless illumination suitable for recognizing surface characteristics of the body or body part to be digitized and a patterned illumination suitable for recognizing the spatial shape of the body and/or body part to be digitized.

The photogrammetric marks may also be optically designed so as to reflect the light of the light pattern projector in a manner which can be automatically distinguished from the reflection of the body and/or body part in the image of the camera using methods of image processing; the light polarization may also be advantageously utilized.

A projected light line 22 extends from the marked surface 10 over the non-marked foot to be digitized up to and beyond the marked band 20. The image field of the camera is designed appropriately by selecting the focal length.

Figure 2:
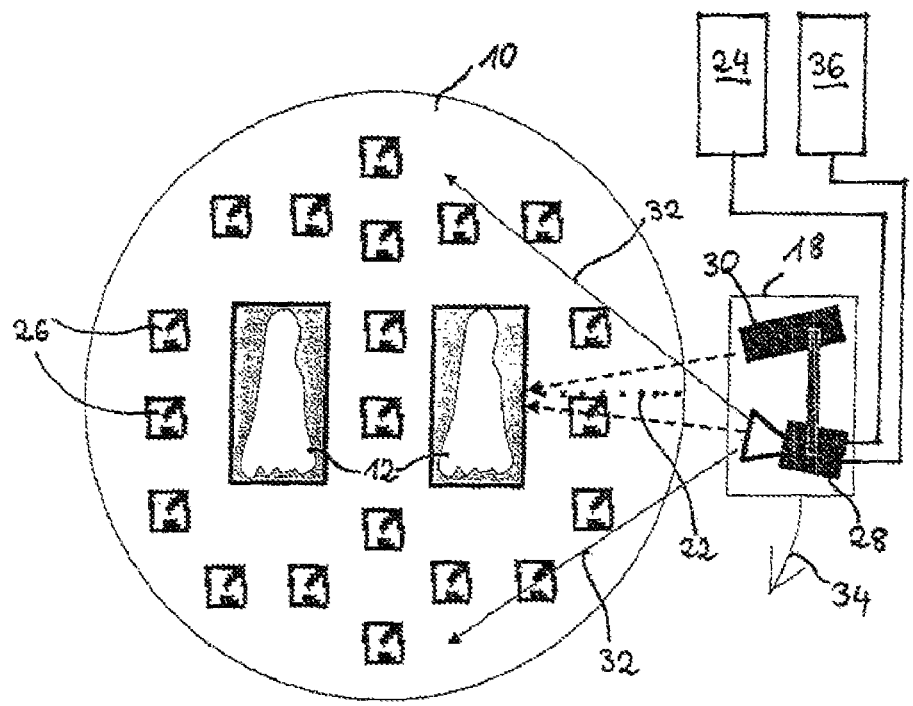
FIG. 2 schematically shows an arrangement according to the invention in a top view.

While the triangulation arrangement 18 (or measuring head) is moved around the patient, a large number of exposures which each form an image of a detail of the marked surface 10, a detail of the foot 12, and also a detail of the marked band 20 are released by an image taking control means 24, which is indicated in FIG. 2. The exposures need to overlap. The smaller the spatial distances between the exposures, the more accurate both the calibration and the digitization will be.

FIG. 2 shows a top view of the marked surface 10 with photogrammetric marks 26, the triangulation arrangement 18 comprising the camera 28 and the light line projector 30, and the light line 22 generated by the light line projector and beginning on the marked surface 10. Two arrows 32 indicate that the camera 28 of the measuring head 18 captures a detail of the marked surface 10. An arrow 34 indicates the direction of movement of the triangulation arrangement. Next to the image taking control means 24 already mentioned above, a computer 36 for evaluating the images taken by the camera is indicated. The feet 12 are shown schematically. Successive images have a large overlap area, so that the photogrammetrically marked marks 26 can be easily located again in the individual images based on an automatic recognition of the coding thereof, and can be assigned to each other. It is known to a person skilled in the art of photogrammetry that all internal and external parameters of the camera, such as absolute position in space, focal length, position of the sensor within the camera, etc., can be determined hereby.

Figure 3:
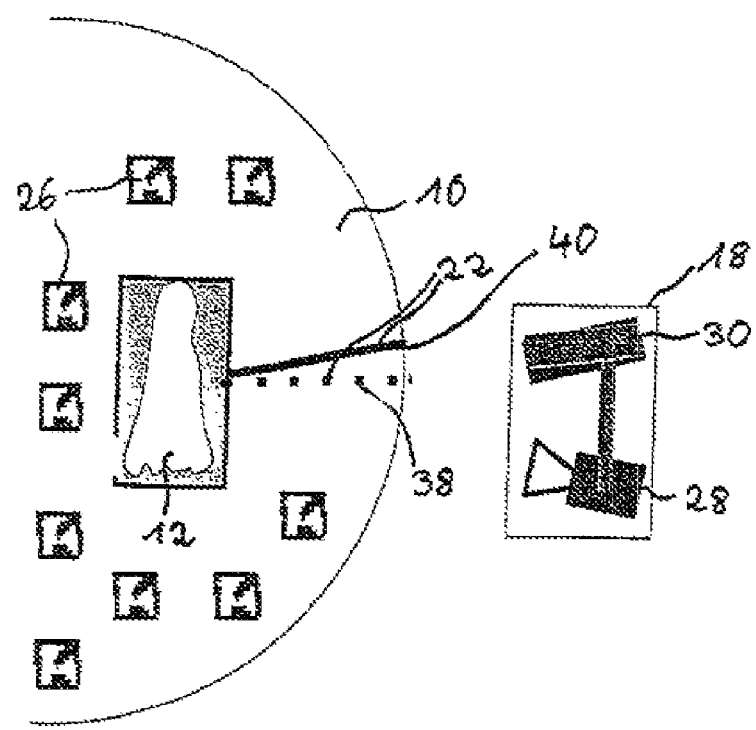
FIG. 3 schematically shows a detail of the arrangement according to FIG. 2, with the light line projector rotated.

FIG. 3 shows a detail of the arrangement from FIG. 2 with the surface 10, a foot 12, marks 26, and the triangulation arrangement 18. A slight rotation of the light line projector 30 is indicated, resulting in a change in the triangulation angle. As already discussed above, the accuracy of the measurement greatly depends on the triangulation angle. The rotation of the light line projector 30 in a plane parallel to the marked surface 10 results in a rotation of the light line 22 from a position 38 to a position 40 on the marked surface 10. This rotated light line is captured by the camera 28; based on the marks 26, the angle of rotation can be determined by evaluation of the images taken.

Figure 4:
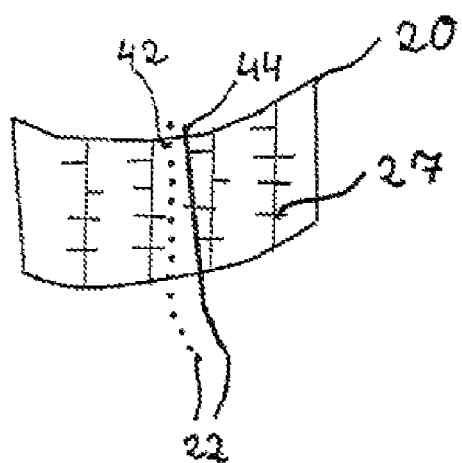
FIG. 4 shows a detail of a marked band according to the invention, with two light line courses.

FIG. 4 schematically shows a detail of the marked band 20 as is visible in the image field of the camera 28. A tilting of the vertical orientation of the light line projector 30 leads to a tilting of the light trace or light line 22 on the marked band 20 from a position 42 to a position 44, which is captured by the camera 28. Here, too, the marks on the band permit the absolute determination of the shift in position.

Under the condition—easy to satisfy in terms of optical design—that the light line projector 30 generates a sufficiently straight line, the computer 36, to which the image data is transferred, can accurately calculate the internal and external parameters of the triangulation arrangement 18 for each taking position by an evaluation of the photogrammetric marks 26 of the surface 10 and of the band 20 as well of the light pattern of the light projector 30 on the marked surface 10 and on the marked band 20, by means of a program for automatic photogrammetric determination.

The automatic recognition of the light line 22 in the image field of the camera 28 is known to a person skilled in the art of image processing. The automatic recognition of the photogrammetric marks 26 on the surface 10 and on the elastic band 20 is known from the products, product specifications, publications and published property rights of the company of corpus.e AG and is part of the general knowledge of a person skilled in the art, and therefore need not be discussed here in more detail.

Although the invention has been described hereinabove with reference to a specific embodiment, it is not limited to this embodiment and no doubt further alternatives will occur to the skilled person that lie within the scope of the invention as claimed.

The invention claimed is:

1. A method for precise optical detection of the 3D spatial shape of bodies or body parts by digital scanning, comprising the steps of:

positioning a body to be scanned or a body part to be scanned on a surface of a base, said surface being marked with photogrammetric marks;

applying photogrammetric marks in a partial area of the body or body part to be scanned;

moving at least one triangulation arrangement around the body or body part to be scanned, the triangulation arrangement including at least one camera and at least one light pattern projector, the triangulation arrangement having internal and external parameters, the at least one camera capturing a sequence of images and the light pattern projector projecting a light pattern onto the body or body part, each captured image including an image field extending from the marked surface over non-marked areas of the body or body part;

the photogrammetric marks being applied on at least one band fitted to the body or body part in a position spaced from said marked surface at a maximum possible distance and such that the photogrammetric marks are captured at least in the majority of captured images; and the image fields of successive captured images overlapping each other;

evaluating the photogrammetric marks of the surface and the photogrammetric marks and the light pattern of the at least one light projector on the marked surface and on the photogrammetric marks in the partial area to determine the internal and external parameters of the at least one triangulation arrangement for each position in which an image was captured; and determining the 3D spatial shape of the body or body part by applying methods of photogrammetry using these parameters and by evaluating the position of the light pattern on the body or body part in the images taken by the at least one camera.

2. The method according to claim 1, wherein said light pattern projector projects a narrow light line and the 3D spatial shape is established by processing reflected light.

3. The method according to claim 1, wherein the camera is color-capable, and colors of the photogrammetric marks of the surface and of the photogrammetric marks of the body or body part as well as the color or colors of the light pattern projector are selected such that they can be recognized and distinguished in the color images of the color camera using methods of color classification.

4. The method according to claim 1, wherein the camera is a black-and-white camera, and at least one of the design of the shape and the brightness of the marks of the surface and of the photogrammetric marks of the body or body part as well as of the light pattern projector are selected such that they can be recognized and distinguished in the gray scale value images of the black-and-white camera using methods of optical pattern recognition.

5. The method according to claim 1, wherein the camera is a color camera, and the colors of the photogrammetric marks of the surface and of the photogrammetric marks of the body or body part as well as the color or colors of the light pattern projector and at least one of the design of the shape and the brightness of the marks of the surface and of the band as well as of the light pattern projector are selected such that they can be recognized and distinguished in the color images of the color camera using methods of optical pattern recognition.

6. The method according to claim 1, wherein the light pattern projector switches over alternately between a patternless illumination suitable for recognizing surface characteristics of the body or body part and a patterned illumination suitable for recognizing the spatial shape of the body or body part.

7. The method according to claim 1, wherein the photogrammetric marks of the surface and the photogrammetric marks of the body or body part are optically designed so as to reflect the light of the light pattern projector in a manner which can be automatically distinguished from the reflection of the body or body part in the image of the camera using methods of image processing.

8. The method according to claim 7, wherein the photogrammetric marks of the surface and the photogrammetric marks of the body or body part affect the polarization of the light pattern from the projector differently from the reflecting body or body part.

9. The method according to claim 1, wherein the triangulation arrangement is guided manually around the body to be digitized.

10. An arrangement for carrying out the method according to claim 1, comprising:
- a base with a marked surface which is provided with photogrammetrically evaluatable marks and on which a body or body part to be digitally scanned can be positioned;
- a triangulation arrangement comprised of a camera and a light pattern projector;
- photogrammetrically evaluatable marks on a carrier which can be fitted to the body or body part in a position farthest away from the marked surface;
- an actuating means for moving the triangulation arrangement around the body or body part; and
- image capturing control means for controlling the capturing of images during movement of the triangulation arrangement, the camera having an image field extending from the marked surface over the body or body part as far as to the photogrammetric marks on the body or body part; and
- a computer to which data from captured images is transferred, the computer including a program for automatic photogrammetric determination of all unknown internal and external parameters of the triangulation arrangement and the spatial shape of the body or body part to be scanned.

11. The arrangement according to claim 10, wherein the carrier is a band or ribbon on which the photogrammetric marks are applied, and the band or ribbon can be fitted to the body or body part.

12. The arrangement according to claim 10, wherein the actuating means is formed by manual movement of the triangulation arrangement.

* * * * *